Figure 1:
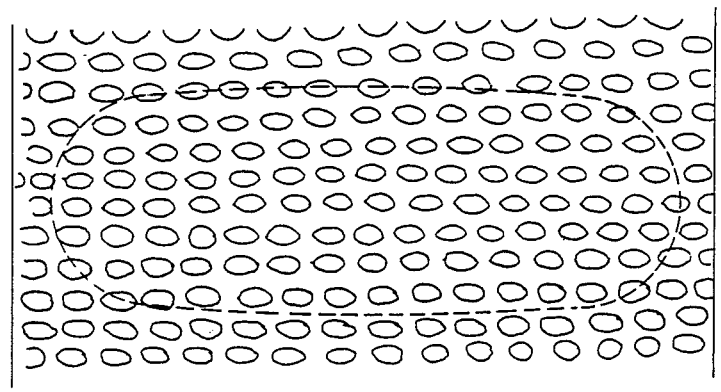
Figure 2:
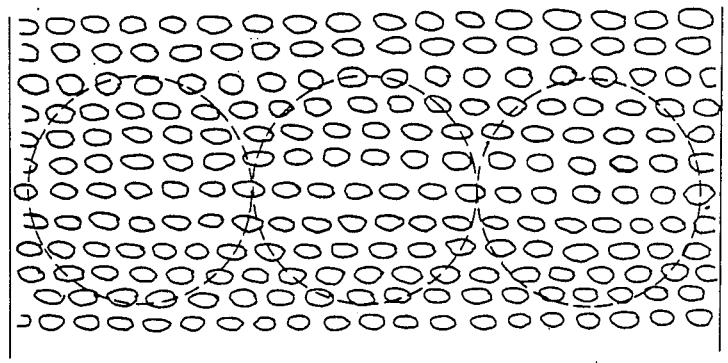

United States Patent [19]
Appelgren

[11] Patent Number: 4,701,341
[45] Date of Patent: Oct. 20, 1987

[54] METHOD FOR COATING GRANULES, PILLS, AND TABLETS

[75] Inventor: Curt H. Appelgren, Kungsbacka, Sweden

[73] Assignee: Lejus Medical Aktiebolag, Molndal, Sweden

[21] Appl. No.: 841,612

[22] Filed: Mar. 20, 1986

[30] Foreign Application Priority Data

Mar. 20, 1985 [SE] Sweden ................... 8501365

[51] Int. Cl.$^4$ .................. A61K 9/00; B05D 1/02; B05D 7/00
[52] U.S. Cl. ...................... 427/3; 427/212; 427/425
[58] Field of Search ............. 427/3, 212, 425

[56] References Cited

U.S. PATENT DOCUMENTS 4,532,155  7/1985  Golant et al. ............. 427/425 X
4,581,242  4/1986  Forster ...................... 427/3

Primary Examiner—Michael R. Lusignan
Attorney, Agent, or Firm—Burns, Doane, Swecker & Mathis

[57] ABSTRACT

The present invention relates to a process for coating granules, pills, tablets and the like for avoiding excess moistening, and for obtaining an optimal coating time, whereby said products are coated with a coating agent dissolved in a solvent, whereby the products while under movement in the form of a bed of products are sprayed with said solution which is added via a series of spraying nozzles, whereby these are placed side by side over the bed of products to be sprayed, and are placed perpendicular to the direction of movement of the bed, whereby the spray pictures are placed in such a way that overlapping of two adjacent spray pictures on the bed is avoided.

4 Claims, 2 Drawing Figures

METHOD FOR COATING GRANULES, PILLS, AND TABLETS

DESCRIPTION

1. Technical Field

The present invention relates to a method for coating granules, pills, and tablets by spraying thereon a coating agent dissolved in a solvent.

The object of the present invention is to obtain an even layer in the coating of granules, pills, and tablets.

2. Background of the Invention

In the spraying of granules, pills, and tablets using a solution of a coating agent, commonly a polymer, dissolved in a solvent, the solution is sprayed towards a moving bed of granules, pills or tablets within, e.g., a rotating coating pan. In order to reduce the zone within which the spraying takes place one has used a so called flat spray. When working with organic solvents a slit-shaped nozzle has been used together with high pressure to obtain the flat spray shape. However, such nozzles have the disadvantage of easily clogging. When changing to water-based, and less volatile solvents, one has therefore developed a flat spray, wherein air is mixed into the solution in order to increase the atomization, whereby one has started the development from a full cone spray, and by controlling, by means of air, e.g., by shunting off a part of the atomizing air, one has compressed the spray shape to a flat spray form, whereby a wide, oval spray form is obtained in the bed. It has, however, turned out that one does not obtain acceptable coating results, when using this spraying method. Above all, one has obtained too high a moisture content appearing locally in the tablet bed, which, in the case of readily soluble tablets, leads to deformation of the tablets, and thereby, in case of identification gravures present thereon, has meant a levelling/elimination of the gravure. Certain tablets change their colour when the become overly moistened. In order to reduce the problem of too high a moisture content one has been forced to reduce the amount sprayed, which however, has led to very long coating times.

DESCRIPTION OF THE PRESENT INVENTION

It has now surprisingly been shown possible to be able to solve the above given problems by means of the present invention, which is characterized in that a series of full conical spray profiles are placed side by side over the bed of particles to be coated, and perpendicular to the direction of movement of the bed, whereby the spray profiles are placed so that an overlap of two adjacent spray profiles is avoided.

Further characteristics are evident from the accompanying claims.

By means of the present invention the coating result is considerably improved, and the above drawbacks are eliminated, and the coating time can be considerably shortened.

The present invention will be described more in detail in the following with reference to the attached drawing, wherein FIG. 1 shows a picture obtained by flat spray according to the prior technique;

FIG. 2 shows a picture obtained by a spraying in accordance with the present invention.

In a rotating coating pan having a bed width of 50 cm five full-conical spray nozzles are arranged onto a stand. The nozzles are provided with conduits for adding spraying solution and air. The spray nozzles are placed about 30 cm above the bed of tablets and in such a way that they are placed adjacent each other, perpendicular to the bed of tablets which is moving and proceeding by means of the rotation. The outlet angle of the nozzles is chosen in such a way that no overlap of two adjacent spray pictures occurs on the bed of tablets.

In FIG. 1 a conventional flat spray pattern comprising 3 spray nozzles for covering a bed of tablets having a width of 50 cm is shown.

In FIG. 2 a spray pattern according to the present invention comprising 3 spray patterns for covering a bed of tablets having a width of 50 cm is shown.

EXAMPLE 1

Using an equipment in accordance with the description above with three adjacent full conical spraying nozzles and spraying a solvent therethrough the following droplet size distribution was obtained when measuring with a Malven ST 2200 laser particle analyzer.

TABLE 1

| Size | Weight in the band at a distance of | | |
|---|---|---|---|
| μm | 120 mm | 160 mm | 200 mm |
| 0.0–5.8 | 29.6 | 31.1 | 27.0 |
| 5.8–7.2 | 3.2 | 3.6 | 5.1 |
| 7.2–9.1 | 7.9 | 7.9 | 7.9 |
| 9.1–11.4 | 12.5 | 14.3 | 13.6 |
| 11.4–14.5 | 20.7 | 18.6 | 20.0 |
| 14.5–18.5 | 18.0 | 16.9 | 17.0 |
| 18.5–23.7 | 8.1 | 7.6 | 9.4 |
| 23.7–30.3 | 0.0 | 0.0 | 0.0 |
| 30.0–564.0 | 0.0 | 0.0 | 0.0 |

EXAMPLE A

The process of Example 1 was repeated with the exception that a flat spray nozzle J930/J29P was used instead.

TABLE 2

| Size | Weight in the band at a distance of | | |
|---|---|---|---|
| μm | 120 mm | 160 mm | 200 mm |
| 0.0–5.8 | 23.9 | 19.4 | 18.4 |
| 5.8–7.1 | 2.2 | 1.9 | 3.0 |
| 7.2–9.1 | 6.2 | 5.2 | 5.0 |
| 9.1–11.4 | 9.4 | 9.2 | 7.7 |
| 11.4–14.5 | 13.5 | 11.8 | 12.8 |
| 14.5–18.5 | 12.7 | 9.6 | 10.4 |
| 18.5–23.7 | 7.7 | 6.4 | 7.0 |
| 23.7–39.0 | 0.0 | 0.0 | 0.0 |
| 39.0–50.2 | 0.0 | 0.1 | 0.5 |
| 50.2–160.4 | 0.0 | 0.0 | 0.0 |
| 160.4–261.6 | 11.3 | 20.5 | 21.1 |
| 261.5–564.0 | 13.1 | 16.0 | 14.1 |

As evident from above a considerable agglomeration of droplets is obtained using the flat spray technique.

Measurement has been made in a greater number of size range bands in the tests above, but for simplicity they have been brought together to broader ranges when the weight was 0.0 in each band at each distance.

I claim:

1. A process for coating granules, pills or tablets with a coating agent dissolved in a solvent comprising:
   (a) moving the articles to be coated perpendicularly past a series of spray nozzles; and
   (b) issuing a full conical spray of the coating agent dissolved in the solvent from the spraying nozzles in a manner such that overlapping of adjacent spray patterns is avoided.

2. The process of claim 1 wherein the articles to be coated are moved in a rotating coating pan.

3. The process of claim 2 wherein the coating pan has a bed width of 50 cm.

4. The process of claim 1 wherein the spray nozzles are placed about 30 cm above the articles to be coated.

* * * * *